(12) United States Patent
Yu et al.

(10) Patent No.: US 12,042,504 B2
(45) Date of Patent: *Jul. 23, 2024

(54) INJECTABLE FOSAPREPITANT COMPOSITION

(71) Applicant: Spes Pharmaceuticals Inc., North Brunswick, NJ (US)

(72) Inventors: Jianwei Yu, Plainsboro, NJ (US); Yulu Wang, Plainsboro, NJ (US)

(73) Assignee: Spes Pharmaceuticals Inc.

( * ) Notice: Subject to any disclaimer, the term of this patent is extended or adjusted under 35 U.S.C. 154(b) by 172 days.

This patent is subject to a terminal disclaimer.

(21) Appl. No.: 17/379,999

(22) Filed: Jul. 19, 2021

(65) Prior Publication Data

US 2022/0062309 A1    Mar. 3, 2022

Related U.S. Application Data

(63) Continuation of application No. 16/245,992, filed on Jan. 11, 2019, now Pat. No. 11,065,265.

(60) Provisional application No. 62/673,522, filed on May 18, 2018.

(51) Int. Cl.
| | | |
|---|---|---|
| *A61K 31/675* | (2006.01) | |
| *A61K 9/00* | (2006.01) | |
| *A61K 9/08* | (2006.01) | |
| *A61K 47/18* | (2017.01) | |
| *A61K 47/40* | (2006.01) | |

(52) U.S. Cl.
CPC .......... *A61K 31/675* (2013.01); *A61K 9/0019* (2013.01); *A61K 9/08* (2013.01); *A61K 47/183* (2013.01); *A61K 47/40* (2013.01)

(58) Field of Classification Search
CPC ...... A61K 31/675; A61K 9/0019; A61K 9/08; A61K 47/183; A61K 47/40; A61K 47/02
USPC ...................................................... 514/9, 300
See application file for complete search history.

(56) References Cited

U.S. PATENT DOCUMENTS 11,065,265 B2 *    7/2021   Yu ............................ A61K 9/08

FOREIGN PATENT DOCUMENTS

WO     WO-2017021880 A1 *    2/2017   ......... A61K 31/5377

* cited by examiner

*Primary Examiner* — Yevgeny Valenrod
(74) *Attorney, Agent, or Firm* — Gearhart Law, LLC

(57) ABSTRACT

The present application and its embodiments teach stable compositions of fosaprepitant or a pharmaceutically acceptable salt thereof with such compositions lacking polysorbate 80 and containing dual functional excipients of hydrolysis inhibition and solubility enhancement. Further described are methods of preparation of such compositions. Among other advantages of contemplated compositions, fosaprepitant hydrolysis degradation is kept low and the compositions maintain physically and chemically stable for prolonged period.

14 Claims, No Drawings

INJECTABLE FOSAPREPITANT COMPOSITION

CLAIM OF PRIORITY

This application claims priority to U.S. Application 62/673,522 filed on May 18, 2018, the contents of which are herein fully incorporated by reference in its entirety.

FIELD OF THE EMBODIMENTS

The field of the present invention and its embodiments relate to stable compositions of fosaprepitant or a pharmaceutically acceptable salt thereof. In particular, the present application relates to the compositions of fosaprepitant dimeglumine which do not contain polysorbate 80 or similar surfactants. The present application further describes methods of preparation of such compositions.

BACKGROUND OF THE EMBODIMENTS

Fosaprepitant dimeglumine is the active pharmaceutical ingredient of EMEND® for Injections marketed by Merck Sharp & Dohme Corp. Fosaprepitant is a water-soluble phosphorylated prodrug of aprepitant, which is rapidly converted to aprepitant in vivo following intravenous (IV) administration. Aprepitant is an antagonist of human substance P neurokinin 1 (NK1) receptors. Thus, the pharmacological activity of fosaprepitant and the anti-emetic effects reflect those of its parent compound, aprepitant.

Aprepitant, the parent compound of fosaprepitant is a white to off-white crystalline solid that has a molecular weight of around 534.53 g. It has a very limited solubility in water, but it does have a reasonably high solubility in non-polar solvents such as oils. This would suggest that aprepitant as a whole, despite having components that are polar, is a non-polar substance. Aprepitant resulting from fosaprepitant hydrolytic degradation may precipitate out from solution and physically appear as the undesirable particulate matter or precipitate in the solution for injection. While it is necessary and an ultimate step for fosaprepitant to be converted to aprepitant in vivo after administered to the patients, any premature conversion of fosaprepitant to aprepitant before being injected into patients could be detrimental.

EMEND® for Injection is currently the only approved injection product of fosaprepitant. The injection comprises a sterile, lyophilized powder formulation containing fosaprepitant dimeglumine. Each vial of EMEND® for Injection contains 150 mg of fosaprepitant (equivalent to 245.3 mg of fosaprepitant dimeglumine) and the following inactive ingredients: 5.4 mg or 18.8 mg of edetate disodium; 75 mg of polysorbate 80; 375 mg of lactose anhydrous; and sodium hydroxide and/or hydrochloric acid may be used for pH adjustment.

Due to the inherent tendency of hydrolysis of fosaprepitant (or its salt) in aqueous environment, fosaprepitant undergoes hydrolytic degradation forming aprepitant, even in solid state as in EMEND® for Injection, a lyophilized powder form of fosaprepitant. Therefore, to prevent potential aprepitant crystallization and precipitation which is formed from hydrolytic degradation of fosaprepitant over product shelf life, EMEND® for Injection is formulated with Polysorbate 80 as a solubilizing agent for aprepitant. However, polysorbate 80, a commonly used solubilizing agent for low solubility drug formulation, is known to cause various adverse reactions, including severe infusion site reactions and the potential life-threatening anaphylactic reactions. In a review of cancer drugs containing polysorbate 80, hypersensitivity reactions were linked to at least 23 deaths despite of the fact that all 23 patients had received premedication to prevent hypersensitivity reactions.

Hypersensitivity reactions that have been reported to be associated with fosaprepitant injections include but are not limited to flushing, erythema, dyspnea, and anaphylaxis. If such symptoms occur, the infusion has to be discontinued and appropriate medical therapy needs to be administered immediately. The infusion in patients who experience these symptoms during first time use should not be re-initiated. Therefore, there is a strong medical need to develop a surfactant free fosaprepitant composition.

For instance. U.S. Pat. No. 9,561,229 pertains to pharmaceutical formulations of aprepitant suitable for parenteral administration including intravenous administration. Also included are formulations including both aprepitant and dexamethasone sodium phosphate. The pharmaceutical formulations are stable oil-in-water emulsions for non-oral treatment of emesis and are particularly useful for treatment of subjects undergoing highly emetogenic cancer chemotherapy.

U.S. Pat. No. 9,913,853 pertains to stable pharmaceutical compositions of fosaprepitant or a salt thereof in the form of ready-to-use or ready-to-dilute compositions suitable for parenteral administration.

U.S. Patent Application 2011/0009362 pertains to solubility-enhanced forms of aprepitant and processes for preparing such forms. The invention also provides solubility-enhanced forms of aprepitant that also possess stability against solid state conversions. Certain solubility-enhanced forms of aprepitant comprise a cyclodextrin or any of its derivatives. Other solubility-enhanced forms of aprepitant comprise fine particle preparations of aprepitant. The invention further provides non-nanoparticulate pharmaceutical formulations prepared using solubility-enhanced forms of aprepitant. The invention also provides taste-masked and orally disintegrating pharmaceutical formulations comprising aprepitant. Further, pharmaceutical formulations comprising solubility enhanced forms of aprepitant and processes of preparation of such formulations, as well as methods of using them are provided.

U.S. Patent Application 2017/0136027 pertains to an aqueous stable and ready-to-use formulation of aprepitant. Especially preferred formulations comprise a synergistic combination of a co-solvent and a surfactant and may further include a secondary co-solvent. Among other advantages of contemplated formulations, aprepitant is dissolved at high concentrations and remains dissolved and stable, even over prolonged periods of time.

International Application WO2016/059587 pertains to a stable, non-aqueous and ready-to-use injectable composition of a pharmaceutically active agent a pharmaceutically active agent or a pharmaceutically acceptable salt or a co-crystal thereof. The present invention also relates to a process for the preparation of the stable, non-aqueous and ready-to-use injectable composition of pharmaceutically active agent involving use of a non-solvent solvent system suitable for preparing a stabilized injectable composition comprising a pharmaceutically active agent a pharmaceutically active agent or a pharmaceutically acceptable salt or a co-crystal thereof. It is not required to reconstitute the injectable composition of pharmaceutically active agent with water prior to administration, thereby rendering it an easy-to-use injectable composition.

International Application WO2017/021880 pertains to the present invention relates to liquid formulations of Fosaprepitant intended for parenteral administration. Further the invention also describes process for preparing such formulations.

Various systems and methodologies are known in the art. However, their structure and means of operation are substantially different from that of the present disclosure. There is no teaching of a stable, polysorbate 80 free aqueous composition comprising fosaprepitant and a dual-functional excipient which play a role in both fosaprepitant hydrolysis inhibition and aprepitant solubility enhancement, which imparts extended storage stability to fosaprepitant in aqueous solution both physically and chemically. The present invention and its embodiments, therefore, provide storage stable aqueous compositions of fosaprepitant free of Polysorbate 80 or other surfactant comprising fosaprepitant or its derivatives and salts, a fosaprepitant hydrolysis inhibiting and aprepitant solubility enhancing dual-functional excipient, in an aqueous vehicle with a defined pH range.

At least one embodiment of this invention is presented in the drawings below and will be described in more detail herein.

SUMMARY OF THE EMBODIMENTS

The present application discloses the utilization of a dual functional excipient to inhibit the hydrolytic degradation of fosaprepitant to the insoluble aprepitant and, in the meantime, solubilize aprepitant formed from fosaprepitant hydrolytic degradation and prevent its crystallization and precipitation from solution, thereby result in extended period of physical and chemical stability of the compositions.

Further, the present invention and its embodiments teach stable liquid compositions of fosaprepitant or a pharmaceutically acceptable salt for use in cancer therapy, wherein the composition maintains both physically and chemically stable for extended period of time, and is suitable as a ready to use aqueous composition for parenteral administration, whereas, ready to use means directly to be administered or administered after proper dilution with an appropriate infusion solution. The present invention and its embodiments further disclose the compositions and methods of preparation of forming such compositions containing effective amounts or ratios of a dual functional agent of hydrolysis inhibition on fosaprepitant hydrolytic degradation to aprepitant and solubility enhancement on aprepitant in aqueous solution. The dual functional agent of hydrolysis inhibition and solubility enhancement is selected from cyclodextrin derivatives. The hydrolysis inhibitory effect of cyclodextrin derivatives is illustrated in Table 1 which shows that increase in amount of cyclodextrin derivative used in fosaprepitant compositions resulted in significantly less amount hydrolytic degradation product of fosaprepitant, aprepitant. Table 2, on the hand, shows that cyclodextrin derivative dramatically enhance the solubility of aprepitant in aqueous medium. When appropriate amount or ratio of fosaprepitant to cyclodextrin derivative is used, the composition show to prevent the drastic hydrolytic degradation of fosaprepitant to aprepitant, and in the meantime, prevent the crystallization and precipitant of aprepitant (Table 3).

TABLE 1

Inhibitory Effect of Cyclodextrin Derivative on Fosaprepitant Hydrolysis

| Cyclodextrin Derivative | Aprepitant Formed Over Time at 40° C. (%) | | |
|---|---|---|---|
| (mg/mL) | Initial | 7 (day) | 14 (day) |
| 0 | 0.095 | 1.018 | 2.278 |
| 32 | 0.109 | 0.777 | 1.775 |
| 64 | 0.109 | 0.642 | 1.439 |
| 128 | 0.091 | 0.558 | 0.564 |

TABLE 2

Solubility Enhancing Effect of Cyclodextrin Derivative on Aprepitant

| Cyclodextrin Derivative (mg/mL) | Increase in Aprepitant Solubility |
|---|---|
| 0 | 0% |
| 32 | 105% |
| 64 | 300% |
| 128 | 748% |
| 160 | 1039% |
| 180 | 1244% |
| 200 | 1322% |
| 255 | 1717% |

TABLE 3

Inhibitory Effect of Cyclodextrin Derivative on Fosaprepitant Hydrolysis

| Additive | Aprepitant Formed from Fosaprepitant Hydrolysis at 40° C. (%) | | | |
|---|---|---|---|---|
| | Initial | | 30 days | |
| With P80 | 0.120 | CCS | 14.440 | CCS |
| No Additive | 0.095 | CCS | 0.199 | Crystalline Precipitate |
| With cyclodextrin derivative | 0.102 | CCS | 1.626 | CCS |

CCS: Clear colorless solution

In one embodiment of the present invention there is a composition comprising: fosaprepitant or a pharmaceutically acceptable salt thereof; a cyclodextrin derivative; a pharmaceutically acceptable carrier; and a pH adjusting agent; wherein the composition does not contain polysorbate 80.

In yet another embodiment of the present invention there is a stable anti-emetic composition suitable for parenteral injection, the composition comprising: fosaprepitant dimeglumine; sulfobutyl ether β-cyclodextrin; edetate disodium; a pharmaceutically acceptable carrier; and a pH adjusting agent; wherein the composition does not contain polysorbate 80; wherein a weight ratio of the fosaprepitant dimeglumine to the sulfobutyl ether β-cyclodextrin is about 1:10 to about 1:255; and wherein a stability of the composition is maintained for at least one month at 40° C..

In yet another embodiment of the present invention there is a method of preparing a stable anti-emetic composition suitable for parenteral injection, the method comprising the steps of: dissolving fosaprepitant or a pharmaceutically acceptable salt thereof in water forming a solution; adding a cyclodextrin derivative to the solution; adjusting a pH of the solution.

It is an object of the present embodiments to provide a ready to use aqueous composition of fosaprepitant or a pharmaceutically acceptable salt thereof comprising fosaprepitant and at least one pharmaceutically acceptable additive in a pharmaceutically acceptable vehicle with a controlled pH, wherein the fosaprepitant composition exhibits excellent both physical and chemical stabilities.

Another object of the present embodiments is to provide a ready to use aqueous composition of fosaprepitant comprising fosaprepitant or a pharmaceutically acceptable salt, such as fosaprepitant dimeglumine, and a cyclodextrin derivative, wherein the aqueous compositions have a pH range from about 8 to 12, preferably from about 9 to 11, more preferably from about 10 to 11.

Another object of the present embodiments is to provide a stable ready to use aqueous composition of fosaprepitant comprising fosaprepitant dimeglumine in an amount from about 1.6 mg/mL to 9.8 mg/mL, more preferably from 1.6 mg/mL to 4.9 mg/mL, and a cyclodextrin derivative selected from the derivatives of β-cyclodextrin, such as sulfobutyl ether β-cyclodextrin, wherein the aqueous compositions have a pH range from about 8 to 12, preferably from about 9 to 11, more preferably from about 10 to 11.

Another object of the present embodiments is to provide a stable ready to use aqueous composition of fosaprepitant comprising fosaprepitant dimeglumine and sulfobutyl ether β-cyclodextrin, wherein the weight ratio of fosaprepitant to sulfobutyl ether β-cyclodextrin is in between about 1:10 to 1:255, preferably from about 1:30 to 1:255, more preferably from 1:30 to 1:85, wherein the aqueous compositions have a pH range from about 8 to 12, preferably from about 9 to 11, more preferably from about 10 to 11, wherein the composition is physically and chemically stable for at least 3 months at 40° C.

It is a further object of the present embodiments to provide a ready to use aqueous composition of fosaprepitant or a pharmaceutically acceptable salt, comprising fosaprepitant and at least one pharmaceutically acceptable additive in a pharmaceutically acceptable vehicle with a controlled pH, wherein the fosaprepitant composition exhibits excellent physical and chemical stabilities, wherein the said composition on storage for up to 3 months at 25° C. continue to exhibit as a clear and colorless solution without visible precipitates and wherein the said composition on storage generates not more than 3.0% (w/w), preferably not more than 1.0%. (w/w), and more preferably not more than 0.8% (w/w) of aprepitant.

Another object of the present embodiments is to provide a stable ready to use aqueous composition of fosaprepitant comprising fosaprepitant dimeglumine, a sulfobutyl ether β-cyclodextrin, edetate disodium or similar, a chelating agent, water for injection, sodium hydroxide and hydrochloric acid for pH adjustment.

Another object of the present embodiments is to provide a process for making a storage stable, ready to use aqueous composition of fosaprepitant suitable for parenteral administration comprising dissolving fosaprepitant or a pharmaceutically acceptable salt thereof in water for injection forming a solution. To this solution, a cyclodextrin derivative, such as sulfobutyl ether β-cyclodextrin is added and stirred to yield a clear solution. Other pharmaceutically acceptable additives or excipients, such as antimicrobial preservatives, buffer agents, and chelating agents, etc. can also be added as appropriate during the entire process familiar to the skilled in the field.

The solution is then adjusted to a target pH using NaOH and/or HCl solutions and brought to the final volume. The final solution is subsequently subjected to sterile filtration, aseptically filled and packed in an appropriate container and closure system.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

The present invention and its embodiments are directed to a liquid composition comprising fosaprepitant or a pharmaceutically acceptable salt thereof, and at least one pharmaceutically acceptable additive or excipient or agent, such as a derivative of a cyclodextrin.

"Carrier materials" or what are also referred to as "carrier" or "vehicle" or "solvent" include any commonly used in pharmaceutics and should be selected on the basis of compatibility and the solubility profile properties of the desired dosage form. Exemplary carrier materials include, e.g., water, polyethylene glycol, propylene glycol, glycerin, alcohol and other pharmaceutically acceptable water miscible solvents.

As used herein, the terms "including," "containing," and "comprising" are used in their open, non-limiting sense.

As used herein, the singular forms "a," "an." and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Concentrations that are given as percentages refer to mass ratios, unless indicated differently.

Aqueous compositions of fosaprepitant or its pharmaceutically acceptable salt, such as dimeglumine salt, according to the invention comprises a stable solution of fosaprepitant with a cyclodextrin derivative, such as sulfobutyl ether β-cyclodextrin sodium salt, wherein the amount of fosaprepitant is from about 1.6 mg/mL to 9.8 mg/mL, more preferably from 1.6 mg/mL to 4.91 mg/mL as fosaprepitant dimeglumine, wherein the weight ratio of fosaprepitant to the cyclodextrin derivative is between about 1:10 to 1:255, preferably about 1:30 to 1:255, more preferably about 1:30 to 1:85 of fosaprepitant to a cyclodextrin derivative with a solution pH controlled between about 8 to 12, preferably between about 9 to 11, more preferably between about 10 to 11. The composition according to the invention demonstrates extended storage stability, both physically and chemically, wherein the total degradation products, mainly the active pharmaceutical ingredient, aprepitant, formed should be not more than 3.0% weight/weight (w/w), preferably not more than 1.0% (w/w), more preferably not more than 0.8% (w/w).

In accordance with one aspect of the present invention and its embodiments, there is a composition comprising:

a) fosaprepitant or a pharmaceutically acceptable salt thereof;

b) a dual functional agent of hydrolysis inhibition and solubility enhancement;

c) a pharmaceutically acceptable vehicle;

d) another optional pharmaceutical additive; and e) pH adjusted to between about 9 to 11.

wherein the relative amount of fosaprepitant and the dual functional agent of hydrolysis inhibition and solubility enhancement are maintained at appropriate ratios.

One of the advantages of the aqueous parenteral composition of the present invention and its embodiments is that the stability of fosaprepitant is substantially improved in aqueous solution. The described aqueous fosaprepitant compositions are substantially more stable than those with polysorbate 80 or without a cyclodextrin derivative when stored at various temperature conditions as exemplified in Table 3.

The aqueous compositions of the present application do not require the use of i) polysorbate 80 or similar compounds; and ii) any organic non-aqueous solvents or co-solvents, as opposed to known teachings to prevent hydrolysis of fosaprepitant or to prevent aprepitant from crystallization and precipitation, and kept in solution state. The compositions according to the present application are cost effective as they do not require the use of techniques such as freeze drying whose operational cost is high. The inventive composition can advantageously be of single dose or multiple dose ready to use or ready for further dilution before administration.

EXAMPLES

For exemplary purposes only, the following are selected examples.

| Example 1 | |
|---|---|
| Component | Concentration (mg/mL) |
| Fosaprepitant dimeglumine | 4.906 |
| Sulfobutyl ether β-cyclodextrin sodium | 63.84 |
| Edetate disodium | 0.375 |
| NaOH/HCl | q.s. pH 8.5 |
| Water for injection | q.s. 1.0 mL |

| Example 2 | |
|---|---|
| Component | Concentration (mg/mL) |
| Fosaprepitant dimeglumine | 1.557 |
| Sulfobutyl ether β-cyclodextrin sodium | 127.68 |
| Edetate disodium | 0.375 |
| NaOH/HCl | q.s. pH 10 |
| Water for injection | q.s. 1.0 mL |

| Example 3 | |
|---|---|
| Component | Concentration (mg/mL) |
| Fosaprepitant dimeglumine | 4.906 |
| Sulfobutyl ether β-cyclodextrin sodium | 127.68 |
| Edetate disodium | 0.375 |
| NaOH/HCl | q.s. pH 10 |
| Water for injection | q.s. 1.0 mL |

| Example 4 | |
|---|---|
| Component | Concentration (mg/mL) |
| Fosaprepitant dimeglumine | 4.906 |
| Sulfobutyl ether β-cyclodextrin sodium | 255.36 |
| Edetate disodium | 0.375 |
| NaOH/HCl | q.s. pH 10 |
| Water for injection | q.s. 1.0 mL |

| Example 5 | |
|---|---|
| Component | Concentration (mg/mL) |
| Fosaprepitant dimeglumine | 9.812 |
| Sulfobutyl ether β-cyclodextrin sodium | 255.36 |
| Edetate disodium | 0.375 |
| NaOH/HCl | q.s. pH 11 |
| Water for injection | q.s. 1.0 mL |

| Example 6 | |
|---|---|
| Component | Concentration (mg/mL) |
| Fosaprepitant dimeglumine | 4.906 |
| Sulfobutyl ether β-cyclodextrin sodium | 63.84 |
| Polyoxyl 35 castor oil | 20.0 |
| Edetate disodium | 0.375 |
| NaOH/HCl | q.s. pH 9.6 |
| Water for injection | q.s. 1.0 mL |

Described herein is an exemplary method of preparation for forming such stable compositions of fosaprepitant: weigh water of about 60-80% of the batch size to be prepared into an appropriate compounding container and bring water to the desired temperature; add batch required amount of fosaprepitant or its pharmaceutically acceptable salt and mix until completely dissolved; followed by adding the batch required amount of cyclodextrin derivative, in increments if necessary, under continuous mixing and mix until all cyclodextrin derivative is completely dissolved and form a homogeneous solution.

Alternatively, such a homogeneous solution can also be formed by first dissolving fosaprepitant and cyclodextrin derivative in two separate parts of the 60-80% water to form two separate parts of clear solutions, and then mixed together the two solutions to form a fosaprepitant and cyclodextrin clear homogenous solution. The solution is adjusted to the desired target pH using NaOH and/or HCl solutions. Additional water is used to bring the total volume to the intended batch size. Without being more specific, skilled to the arts in the field, other optional excipients can also be incorporated into the batch during the entire process without limitation. Final product solution is filtered through a 0.22 μm sterile filter and filled into pre-sterilized container closure system under protection. Compositions prepared by the method exhibit extended physical and chemical stabilities, and are exemplified and illustrated in Table 4

TABLE 4

Physical Stability of Fosaprepitant Formulations at 40° C.

| SBECD (%) | Time (month) | | | |
|---|---|---|---|---|
| | 0 | 0.25 | 0.5 | 1 |
| With P80 | CCS | CCS | CCS | CCS |
| 0 | CCS | CCS | CCS | Precipitate |
| 3.2 | CCS | CCS | CCS | CCS |
| 6.4 | CCS | CCS | CCS | CCS |
| 12.8 | CCS | CCS | CCS | CCS |

CCS: clear and colorless solution

TABLE 5

Aprepitant (%) Formed in Fosaprepitant Solutions at Different Storage Conditions

| SBECD (%) | Storage Temp. | Time (month) | | | | | |
|---|---|---|---|---|---|---|---|
| | | 0 | 0.25 | 0.5 | 1 | 2 | 3 |
| 0 | 5° C. | 0.095 | NA | NA | 0.114 | 0.125 | 0.143 |
| | 25° C. | 0.095 | 0.171 | 0.291 | 0.485 | 0.939 | 0.179* |
| 3.2 | 5° C. | 0.109 | NA | NA | 0.123 | 0.145 | 0.127 |
| | 25° C. | 0.109 | 0.175 | 0.255 | 0.408 | 0.705 | 0.936 |
| 6.4 | 5° C. | 0.109 | NA | NA | 0.126 | 0.126 | 0.130 |
| | 25° C. | 0.109 | 0.158 | 0.225 | 0.348 | 0.604 | 0.772 |
| 12.8 | 5° C. | 0.091 | NA | NA | 0.118 | 0.119 | 0.114 |
| | 25° C. | 0.091 | 0.141 | 0.203 | 0.306 | 0.522 | 0.727 |

*Aprepitant precipitation occurred. All others are CCS
NA: No test was scheduled.

*: Aprepitant precipitation occurred. All others are CCS
NA: No test was scheduled.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method for preventing or treating a subject at risk of or suffering from nausea and vomiting, the method comprising the step of:
   administering to the subject a composition comprising a physicochemically stable injectable aqueous solution, wherein the physicochemically stable injectable aqueous solution comprises:
      fosaprepitant or a pharmaceutically acceptable salt thereof;
      at least one pharmaceutically acceptable derivative of β-cyclodextrin;
      a pharmaceutically acceptable carrier;
      a pH adjusting agent;
   wherein the composition does not contain polysorbate 80;
   wherein a weight ratio of the fosaprepitant or a pharmaceutically acceptable salt thereof to the at least one pharmaceutically acceptable derivative of β-cyclodextrin is about 1:13 to about 1:255; and
   wherein a stability of the stable, liquid composition is maintained for at least three months at 25° C. wherein a pH of the physicochemically stable injectable aqueous solution is adjusted to about 9 to about 11.

2. The method of claim 1 wherein the physicochemically stable injectable aqueous solution further comprising at least one pharmaceutical additive.

3. The method of claim 1 wherein the fosaprepitant is fosaprepitant dimeglumine.

4. The method of claim 3 wherein the fosaprepitant dimeglumine is present in an amount of about 1.6 mg/mL to about 9.8 mg/mL.

5. The method of claim 1 wherein at least one pharmaceutically acceptable derivative of β-cyclodextrin is a sulfobutyl ether β-cyclodextrin sodium salt.

6. The method of claim 1 wherein the physicochemically stable injectable aqueous solution is physically and chemically stable for at least three months at 25° C.

7. The method of claim 6 wherein after three months maintains physically stable and precipitate-free when the total degradation products of the physicochemically stable injectable aqueous solution are about 1.0% (w/w).

8. The method of claim 7 wherein the total degradation products comprise mainly aprepitant.

9. A stable anti-emetic composition suitable for parenteral injection, the composition comprises:
   fosaprepitant or a pharmaceutically acceptable salt thereof;
   at least one pharmaceutically acceptable derivative of β-cyclodextrin;
   a pharmaceutically acceptable carrier; and
   a pH adjusting agent,
   wherein a pH of the composition is adjusted to about 9 to about 12;
   wherein a weight ratio of the fosaprepitant or a pharmaceutically acceptable salt thereof to the at least one pharmaceutically acceptable derivative of β-cyclodextrin is about 1:20 to about 1:85.

10. The composition of claim 9 wherein the pH is adjusted to about 9 to about 11.

11. The composition of claim 9 wherein after three months at 25° C. the stable anti-emetic composition maintains physical stability when the stable anti-emetic composition contains about 1.0% (w/w) of aprepitant.

12. The composition of claim 9 further comprising at least one chelating agent.

13. The composition of claim 12 wherein the at least one chelating agent is aminopolycarboxylic acid or salt thereof.

14. The method of claim 1, wherein the composition further comprises edetate disodium.

* * * * *